United States Patent
Girouard et al.

(10) Patent No.: US 10,143,415 B2
(45) Date of Patent: Dec. 4, 2018

(54) METHOD OF MONITORING A PATIENT FOR SEIZURE ACTIVITY AND EVALUATING SEIZURE RISK

(71) Applicant: Brain Sentinel, Inc., San Antonio, TX (US)

(72) Inventors: Michael R. Girouard, San Antonio, TX (US); Jose E. Cavazos, San Antonio, TX (US); Luke E. Whitmire, San Antonio, TX (US)

(73) Assignee: BRAIN SENTINEL, INC., San Antonio, TX (US)

( * ) Notice: Subject to any disclaimer, the term of this patent is extended or adjusted under 35 U.S.C. 154(b) by 520 days.

(21) Appl. No.: 14/816,924

(22) Filed: Aug. 3, 2015

(65) Prior Publication Data

US 2016/0029947 A1   Feb. 4, 2016

Related U.S. Application Data

(60) Provisional application No. 62/032,147, filed on Aug. 1, 2014, provisional application No. 62/050,054, filed on Sep. 12, 2014, provisional application No. 62/096,331, filed on Dec. 23, 2014, provisional application No. 62/149,434, filed on Apr. 17, 2015.

(51) Int. Cl.
*A61B 5/00* (2006.01)
*A61B 5/04* (2006.01)
*A61B 5/0488* (2006.01)

(52) U.S. Cl.
CPC .......... *A61B 5/4094* (2013.01); *A61B 5/0488* (2013.01); *A61B 5/7275* (2013.01); *A61B 5/002* (2013.01); *A61B 5/0022* (2013.01); *A61B 5/746* (2013.01); *A61B 5/747* (2013.01)

(58) Field of Classification Search
CPC .... A61B 5/4094; A61B 5/4088; A61B 5/7275
See application file for complete search history.

(56) References Cited

U.S. PATENT DOCUMENTS

| | | | | |
|---|---|---|---|---|
| 2010/0137735 A1* | 6/2010 | Hoppe | | A61B 5/0002 600/546 |
| 2012/0083700 A1* | 4/2012 | Osorio | | A61B 5/0245 600/483 |
| 2012/0083701 A1* | 4/2012 | Osorio | | A61B 5/4094 600/483 |
| 2012/0108999 A1* | 5/2012 | Leininger | | A61B 5/0004 600/546 |
| 2012/0116183 A1* | 5/2012 | Osorio | | A61B 5/4094 600/301 |
| 2012/0226108 A1* | 9/2012 | Osorio | | A61B 5/4094 600/301 |
| 2012/0310050 A1* | 12/2012 | Osorio | | A61B 5/4094 600/300 |
| 2013/0012830 A1* | 1/2013 | Leininger | | A61B 5/0488 600/546 |

* cited by examiner

*Primary Examiner* — Jeffrey G Hoekstra
*Assistant Examiner* — Nicholas E Kolderman
(74) *Attorney, Agent, or Firm* — Pizarro Allen PC (57) ABSTRACT

Patients afflicted by a seizure may be monitored for the presence of post-ictal motor manifestations that may indicate that the patient is at heightened risk of adverse effects of a seizure, including, for example, risk of sudden explained death in epilepsy. If the patient is deemed to be at risk of experiencing adverse effects of a seizure, one or more system responses may be initiated as appropriate for the at-risk patient.

20 Claims, 6 Drawing Sheets

METHOD OF MONITORING A PATIENT FOR SEIZURE ACTIVITY AND EVALUATING SEIZURE RISK

CROSS REFERENCE TO RELATED APPLICATIONS

This application claims priority to U.S. Provisional Patent Application No. 62/032,147 filed Aug. 1, 2014, U.S. Provisional Patent Application No. 62/050,054 filed Sep. 12, 2014, U.S. Provisional Patent Application No. 62/096,331 filed Dec. 23, 2014, and U.S. Provisional Patent Application No. 62/149,434 filed Apr. 17, 2015. The disclosures of all of the foregoing applications are herein fully incorporated by reference.

BACKGROUND

A seizure may be characterized as abnormal or excessive synchronous activity in the brain. At the beginning of a seizure, neurons in the brain may begin to fire at a particular location. As the seizure progresses, this firing of neurons may spread across the brain, and in some cases, many areas of the brain may become engulfed in this activity. Seizure activity in the brain may cause the brain to send electrical signals through the peripheral nervous system to different muscles the activation of which may manifest as an electrical signal at the surface of the skin near a muscle.

Techniques designed for studying and monitoring seizures have typically relied upon electroencephalography (EEG), which characterizes electrical signals using electrodes attached to the scalp or head region of a seizure prone individual or seizure patient. Detecting an epileptic seizure using electroencephalography (EEG) typically requires attaching many electrodes and associated wires to the head and using amplifiers to monitor brainwave activity. The multiple EEG electrodes may be very cumbersome and generally require some technical expertise to apply and monitor. Confirmation of a seizure typically requires observation in an environment provided with video monitors and video recording equipment. Furthermore, when measuring brain activity with EEG, not all measured activity of or relating to a seizure may actually be manifested as an event that is likely to be dangerous. And, EEG data without video corroboration may not be suited to grade or differentiate some seizures, including those that may be weak or only of minimal concern, from other seizures that may be more dangerous.

Unless used in a staffed clinical environment, EEG equipment is frequently not intended to determine if a seizure is in progress but rather provide a historical record of the seizure after the incident. EEG equipment is usually designed for hospital-like environments where a video camera recording or caregiver's observation may provide corroboration of the seizure, and is typically used as part of a more intensive care regimen such as a hospital stay for patients who experience multiple seizures. A hospital stay may be required for diagnostic purposes or to stabilize a patient until suitable medication can be administered. Upon discharge from the hospital, a patient may be sent home with little further monitoring.

A patient should in some cases be monitored at home for some length of time in case another seizure should occur. Seizures with motor manifestations may have patterns of muscle activity that include rhythmic contractions of some, most, or all of the muscles of the body. A number of health concerns may develop from this activity. A seizure could, for example, result in Sudden Unexplained Death in Epilepsy (SUDEP). The underlying causes of SUDEP are not well understood; however, in some cases, severe central nervous system (CNS) depression may follow a seizure. Following central nervous system depression, breathing rates may increase and decrease in a cycle that may result in cardiac dysrhythmia and death. However, not all seizures have the same likelihood of causing or being associated with SUDEP, and in some patients, some seizure activity may be present without significant risk of SUDEP. And, without differentiation of seizures by type, severity or further classification, it may be difficult to selectively identify seizure activity that is most likely to be dangerous.

While there presently exist ambulatory devices for diagnosis of seizures, they are EEG-based and are generally not designed or suitable for long-term home use or daily wearability. Other seizure alerting systems may operate by detecting motion of the body, usually the extremities. Such systems may generally operate on the assumption that while suffering a seizure, a person will move erratically and violently. However, depending upon the type of seizure, this assumption may or may not be true. Electrical signals sent from the brain during the seizure are frequently transmitted to many muscles simultaneously, which may result in muscles fighting each other and effectively canceling out violent movement. In other words, the muscles may work to make the person rigid rather than cause actual violent movement. Thus, seizure activity may not be consistently detected with accelerometer-based detectors.

Accordingly, there is a need for seizure detection methods and apparatuses that can be used in non-institutional or institutional environments without many of the cumbersome electrodes to the head or extremities and that accurately detect seizure events with motor manifestations. There is also a need for epileptic seizure detection methods that differentiate weak motor manifestation that may not demand an emergency response from other types of seizures including those that may demand emergency intervention.

SUMMARY

A method of monitoring a patient for seizure activity and analyzing the patient for risk of adverse effects of the seizure activity may include monitoring the patient by collecting an EMG signal and processing of the collected EMG signal to determine whether one or more seizure characteristics may be present. A response may be initiated if the one or more seizure characteristics are found to be present, and in some embodiments, that response may include execution of one or more transmission protocols including protocols that may be automatically selected based on a determined seizure type and/or severity. The collected EMG signal may further be processed to determine a level of motor manifestations in one or more post-ictal time periods. An additional response or updating of a previously issued response may be made if levels of post-ictal motor manifestations indicative of an increased risk of adverse effects of a seizure are detected.

DETAILED DESCRIPTION

The following terms as used herein should be understood to have the indicated meanings.

The term "ambulance transmission protocol" refers to a transmission protocol where an emergency message is sent or predetermined to be sent to an emergency medical technician (EMT) caregiver, with instructions to actively move to the patient's location in order to determine if the patient needs medical treatment.

"Computer" means any programmable machine capable of executing machine-readable instructions. A computer may include but is not limited to a general purpose computer, microprocessor, computer server, digital signal processor, or a combination thereof. A computer may comprise one or more processors, which may comprise part of a single machine or multiple machines.

The term "computer program" means a list of instructions that may be executed by a computer to cause the computer to operate in a desired manner.

The term "computer readable medium" means an article of manufacture having a capacity for storing one or more computer programs, one or more pieces of data, or a combination thereof. A computer readable medium may include but is not limited to a computer memory, hard disk, memory stick, magnetic tape, floppy disk, optical disk (such as a CD or DVD), zip drive, or combination thereof.

The term "emergency transmission protocol" refers to a transmission protocol where an emergency message is sent or predetermined to be sent to a caregiver, including, by way of nonlimiting example, an EMT caregiver, local caregiver, other caregiver, or combinations of caregivers thereof, with instructions to actively move to the patient's location in order to determine if the patient needs medical treatment.

The term "local caregiver" refers to a caregiver who resides permanently or temporarily at a patient's residence.

The term "predetermined message" refers to a message that is scheduled to be sent after some period of time to a caregiver unless intervening instructions are given to prevent sending the message. An intervening instruction to prevent sending of the message may, for example, be provided by another caregiver or may be provided automatically in response to detection of one or more characteristics of sensor data.

"Routine" refers to a method or part of a method that may be executed to monitor a patient for seizure activity. A routine may be run individually in a strategy for monitoring a patient or may be run in combination with other routines in an overall strategy for patient monitoring.

The term "warning transmission protocol" means a transmission protocol that does not by itself (e.g., without other caregiver action or detection of other EMG data) include instructions being provided to a caregiver to actively move to the patient's location in order to physically assist the patient if needed.

The apparatuses and methods described herein may be used to detect seizures and timely alert caregivers of seizure-related events and may further be used to provide early indication that a detected seizure event poses certain risks of adverse effects including SUDEP. The apparatuses may include sensors attached to a patient or patient's clothing and may be configured for measurement of muscle electrical activity using electromyography (EMG). In some embodiments, apparatuses herein may include one or more processors suitable to receive an EMG signal and process the information to detect seizure or seizure-related signals and to analyze the signals for signs of normal or abnormal seizure recovery. Detection of seizures using EMG electrodes is further described, for example, in Applicant's U.S. patent application Ser. Nos. 13/275,309 and 13/542,596 and Applicant's U.S. Provisional Patent Application Nos. 61/875,429, 61/894,793, 61/969,660, 61/979,225, and 62/001,302 the disclosures of each of which are herein fully incorporated by reference. As described in this disclosure, in some embodiments, patients afflicted by a seizure may be monitored for the presence of warning signs that may indicate that the patient is at heightened risk of adverse effects of a seizure, including, for example, risk of SUDEP. In some embodiments, if a patient is deemed to be at risk of experiencing adverse effects of a seizure, one or more system responses may be initiated as appropriate for the at-risk patient.

In some embodiments, assessment of risk of adverse effects of a seizure and the selection of one or more suitable caregiver or system responses may be based on detection of seizure activity and identification of seizure type, determination of the seizure's severity, detection of patient motor manifestations during a period of seizure recovery, other considerations, and/or combinations thereof. A response may, by way of nonlimiting example, include execution of one or more transmission protocols, execution of one or more patient monitoring routines, or may include a combination of both. Responses may further, in some embodiments, be staged and/or updated as information is collected over time. For example, in response to detection of seizure activity an alarm message may be sent to a caregiver or one or more calibration or other monitoring routines may be initiated. For example, a monitoring routine may be initiated that examines EMG signals for the presence of non-seizure movement and/or for a level of motor manifestations typically found during post-seizure periods. And, if, for example, motor manifestations are then identified that reflect characteristics of abnormal or dangerous post-seizure recovery, a new alarm message may be sent or another response may be initiated. A "motor manifestation" may, in some embodiments, generally refer to muscle activity, whether sustained or otherwise. A motor manifestation may, in some embodiments, include electrical activity associated with muscle activity resulting in overt movement of a patient's body or may include electrical activity that does not result in overt movement. For example, included among muscle activity that may not result in overt movement of muscle is some activity used to maintain a level of muscle tone. In some embodiments, levels of muscle electrical activity measured herein may include identifying a level of activity suitable to maintain a level of muscle tone. In some embodiments, those levels may be compared against normal or abnormal levels typical for a patient or patient demographic.

To monitor a patient for seizure activity and/or for the presence of warning signs of adverse effects of a seizure, a monitoring routine may include analysis of EMG signals for patient motor manifestations or muscle activity during the ictal-phase of seizure activity, and in some embodiments, a monitoring routine may also analyze EMG signals collected during periods following detection of seizure activity for a level of motor manifestations. For example, if levels of patient motor manifestations are detected that indicate that the patient may be experiencing central nervous system depression, the patient may be deemed to be at risk of adverse effects of a detected seizure including SUDEP. Some of the embodiments herein may be configured to coordinate an alarm response based not only on increased levels of muscle motor manifestations as may be typically found during a seizure but also on levels of motor manifestations following seizure detection. Routines that may be executable and suited for identification of post-ictal motor manifestations may, in some embodiments, run continuously, semi-continuously, or may be executed in response to detected events including, for example, detected seizure activity. And, for some of those routines, execution in response to detected events may help limit the risk of inadvertent triggering of false alarm responses.

In some embodiments, a seizure detection routine may include analyzing a group of EMG signals for signal features that may indicate the presence of ictal-phase seizure activity and may use those signals to stratify detected events and determine a risk of possible adverse effects of a seizure. Based on an assessment of risk, any of various response protocols may be initiated. For example, in some embodiments and/or for some patients, not all detected signal features, including those that may indicate the presence of ictal-phase seizure activity, may initiate a protocol wherein an ambulance is sent to the patient or always give instructions that a caregiver should check on the patient. For example, some events may be detected, but classified as being of low risk. Also by way of example, a possible response to such a detection may include sending a message to a remote caregiver that a low risk event was detected or it may be determined that the event may simply warrant being logged for post-hoc review.

In some embodiments, a response to a detected event may include initiation of one or more protocols or routines that may execute without active participation by a caregiver. For example, in some embodiments, a caregiver may not be contacted or disturbed as part of the response. In some embodiments, a response may execute without knowledge of a patient and/or a patient and one or more caregivers. A response that is configured to execute without disturbing a patient may herein be referred to as a "passive response." By way of nonlimiting example, some responses that may execute passively include logging an event for post-hoc review, execution of one more calibration routines, and execution of one or more routines to examine an EMG signal for non-seizure activity. In contrast to a passive response, an active response may be executed in which attempts may be made to contact the patient or physically check on the patient. For example, an active response may include calling the patient or sending a caregiver to the patient's physical location to check on the patient and see if the patient needs medical care or attention.

Some of the methods herein may be particularly beneficial for some patients that may experience numerous low-grade seizure or seizure related events. Those events may be detected by analyzing a first group of EMG signals. If the detected events are properly categorized, responses may sometimes appropriately involve actions without disturbing the patient. For example, some seizure or seizure related events may be detected while a patient is resting in bed and those events may, if properly categorized, be properly responded to without waking the patient or without waking the patient and a caregiver. Active responses which may be inconvenient and/or costly may be avoided. However, even for low-grade seizure events, it may still be desirable to have a fail-safe protocol to treat rare, but potentially life-threatening events. Monitoring a patient by collecting a second group of EMG signals and analyzing those signals for the presence of post-ictal signatures of muscle activity may, in some embodiments, facilitate the detection of those rare, but potentially serious events. For example, in some embodiments, a first group of EMG signals may initiate a passive response in response to seizure detection, but when followed by a second group of EMG signals with identification of certain signal features an active response may be initiated. For example, a second group of EMG signals may be analyzed for the presence of abnormal post-seizure recovery, and if such a recovery is indicated an active response may be initiated.

Figure 1:
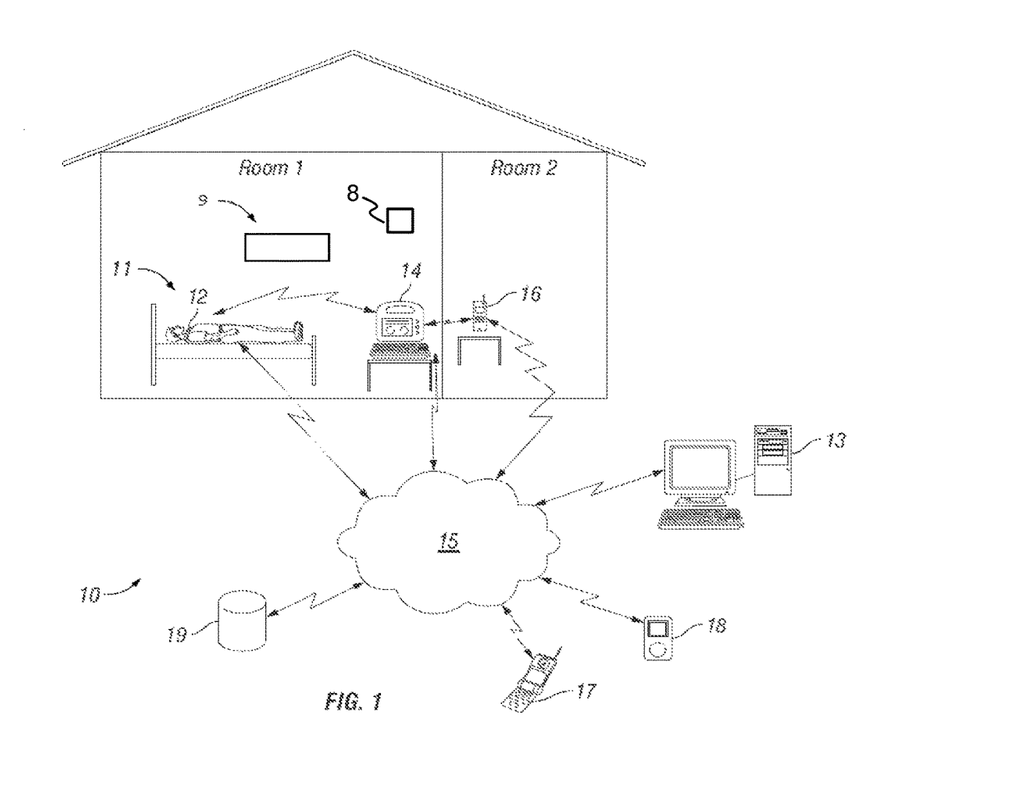
FIG. 1 illustrates one embodiment of a seizure detection system.

A variety of systems may be suitable for collecting large amounts of EMG and other patient-related data, organizing such data for system optimization, and for initiating an alarm in response to a suspected seizure and/or adjusting a response based on post-ictal motor manifestations. FIG. 1 illustrates an exemplary embodiment of such a system that may be configured to monitor a patient for seizure activity using the methods described herein. In the embodiment of FIG. 1, a seizure detection system 10 may include a detection unit 12. The detection unit may be configured as a portable and wearable device disposed on or near (or even attached to) any suitable muscle or muscle groups that may be subject to motor manifestations during a seizure. And, in some embodiments, the system 10 may include any of various wireless local area network technologies. For example, a detection unit 12 may communicate wirelessly to the internet using WiFi, Bluetooth, or through another local network. And, using a local network a detection unit 12 may, in some embodiments, send data over the internet directly or via an intermediate base station 14. In some embodiments, a caregiver may be contacted directly through a local network such as WiFi. A base station 14 may be connected to the internet wirelessly (such as through a local network), or may be linked to the internet through a hard connection. And, in some embodiments, in addition to a detection unit 12 or in addition to a detection unit 12 and base station 14, a system 10 may, for example, include any of an acoustic sensor 8, a video camera 9, alert transceiver 16, or combination of the aforementioned elements. The detection unit may comprise one or more EMG electrodes capable of detecting electrical signals from muscles at or near the skin surface of a patient, and delivering those electrical EMG signals to a processor for processing. The EMG electrodes may be coupled or attached to a patient, and may, in some embodiments, be implanted within the tissue of a patient near a muscle that may be activated during a seizure. Implanted devices may, for example, be particularly amenable for some patients where EMG signals may typically be weak such as patients with significant adipose tissue. The base station 14 may comprise a computer capable of receiving and processing EMG signals from the detection unit, acoustic data from acoustic sensor 8, and/or data from other sensors, determining from the processed signals whether a seizure may have occurred, and sending an alert to a caregiver. An alert transceiver 16 may be carried by, or placed near, a caregiver to receive and relay alerts transmitted by the base station 14 or to the internet. Other components that may be included in the system 10, including for example, wireless communication devices 17, 18, storage database 19, electronic devices for detecting changes in the integrity of an electrode skin interface, and one or more environmental transceivers are also described in Applicant's U.S. patent application Ser. Nos. 13/275,309 and 13/542,596 and Applicant's Provisional Application Nos. 61/894,793 and 61/875,429.

In using the apparatus of FIG. 1, for example, a person 11 susceptible to epileptic seizures may be resting in bed, or may be at some other location as daily living may include, and may have a detection unit 12 in physical contact with or in proximity to his or her body. The detection unit 12 may be a wireless device so that a person may be able to get up and walk around without having to be tethered to an immobile power source or to a bulkier base station 14. For example, the detection unit 12 may be woven into a shirt sleeve, may be mounted to an armband or bracelet, or may be an implanted device. In other embodiments, one or more detection units 12 or other sensors may be placed or built into a bed, a chair, an infant car seat, or other suitable clothing, furniture, equipment and accessories used by those susceptible to seizures. The detection unit 12 may comprise a simple sensor, such as an electrode, that may send signals to the base station 14 for processing and analysis, or may comprise a "smart" sensor having some data processing and storage capability. A detection unit 12 may include one or more smart client applications. In some embodiments, a simple sensor may be connected via wire or wirelessly to a battery-operated transceiver mounted on a belt or other garment or accessory worn by the person.

The system may monitor the patient, for example, while resting, such as during the evening and nighttime hours. If the detection unit 12 on the patient detects a seizure, the detection unit 12 may communicate via wire or wirelessly, e.g., via a communications network or wireless link, with the base station 14, to a remote cell phone or other hand held or desktop device via Bluetooth or other signal or simultaneously to a base station 14 and remote cell phone or other device. In some embodiments, a detection unit 12 may send some signals to the base station 14 for further analysis. For example, the detection unit 12 may process and use EMG signals (and optionally or additionally, or in some embodiments, ECG, temperature, orientation sensors, saturated oxygen, and/or audio sensor signals) to make an initial assessment regarding the likelihood of occurrence of a seizure, and may send those signals and its assessment to the base station 14 for separate processing and confirmation. If the base station 14 confirms that a seizure is likely occurring, then the base station 14 may initiate an alarm for transmission over the network 15 to alert a designated individual by way of email, text, phone call, or any suitable wired or wireless messaging indicator. It should be appreciated that the detection unit 12 may, in some embodiments, be smaller and more compact than the base station and it may be convenient to use a power supply with only limited strength. Therefore, it may be advantageous, in some embodiments, to control the amount of data that is transferred between the detection unit 12 and the base station 14 as this may increase the lifetime of any power supply elements integrated in or associated with the detection unit 12. In some embodiments, if one or more of the detection unit 12, the base station 14, or a caregiver, e.g., a remotely located caregiver monitoring signals provided from the base station 14, determines that a seizure may be occurring, a video monitor 9 may be triggered to collect video information of the patient.

The base station 14, which may be powered by a typical household power supply and contain a battery for backup, may have more processing, transmission, and analysis power available for its operation than the detection unit 12, and may be able to store a greater quantity of signal history and evaluate a received signal against that greater amount of data. The base station 14 may communicate with an alert transceiver 16 located remotely from the base station 14, such as in the bedroom of a family member, or to a wireless device 17, 18 carried by a caregiver or located at a work office or clinic. The base station 14 and/or transceiver 16 may send alerts or messages to designated people via any suitable means, such as through a network 15 to a cell phone 17, PDA 18 or other client device. The system 10 may thus provide an accurate log of seizures, which may allow a patient's physician to understand more quickly the success or failure of a treatment regimen. Of course, the base station 14 may simply comprise a computer having installed a program capable of receiving, processing and analyzing signals as described herein, and capable of transmitting an alert. A base station 14 may include one or more smart client applications. In other embodiments, the system 10 may simply comprise, for example, EMG electrodes as part of a device configured to transmit signal data to a smartphone, such as an iPhone, configured to receive EMG signals from the electrodes for processing the EMG signals as described herein using an installed program application. In further embodiments, so-called "cloud" computing and storage may be used via network 15 for storing and processing the EMG signals and related data. In yet other embodiments, one or more EMG electrodes could be packaged together as a single unit with a processor capable of processing EMG signals as disclosed herein and sending an alert over a network. In other words, the apparatus may comprise a single item of manufacture that may be placed on a patient and that does not require a base station or separate transceiver. Or the base station may be a smartphone or tablet, for example.

In the embodiment of FIG. 1, the signal data may be sent to a remote database 19 for storage. In some embodiments, signal data may be sent from a plurality of patients with epilepsy to a central database 19 and "anonymized" to provide a basis for establishing and refining generalized "baseline" sensitivity levels and signal characteristics of an epileptic seizure. The database 19 and base station 14 may be remotely accessed via network 15 by one or more remote computers 13 to allow updating of detector unit and/or base station software, and data transmission. And, in some embodiments, the remote computer 13 or another computer may also serve to monitor exchange of data including alarm signals and EMG signal data between different devices associated with any number of designated individuals set to receive the signal. The base station 14 may generate an audible alarm, as may a remote transceiver 16 or detection unit 12. All wireless links may be two-way for software and data transmission and message delivery confirmation. The base station 14 may also employ one or all of the messaging methods listed above for seizure notification. The base station 14 or detection unit 12 may provide an "alert cancel" button to terminate an incident warning.

In some embodiments, a transceiver may additionally be mounted within a unit of furniture or some other structure, e.g., an environmental unit or object. If a detection unit 12 is sufficiently close to that transceiver, such a transceiver may be capable of sending data to a base station 14. Thus, the base station 14 may be aware that information is being received from that transceiver, and therefore base station 14 may identify the associated environmental unit. In some embodiments, a base station 14 may select a specific template file, e.g., such as including threshold values and other data as described further herein, that is dependent upon whether or not it is receiving a signal from a certain transceiver. Thus, for example, if the base station 14 receives information from a detector and from a transceiver that is associated with a bed or crib, it may treat the data differently than if the data is received from a transceiver associated with another environmental unit, such as, for example, clothing typically worn while an individual may be exercising or an item close to a user's sink where for example a patient may brush his or her teeth. More generally, a monitoring system may, in some embodiments, be configured with one or more elements with global positioning (GPS) capability, and position information may be used to adjust one or more routines that may be used in a detection algorithm. For example, GPS capability may be included along with or among one or more microelectromechanical sensor elements included in a detection unit.

The embodiment of FIG. 1 may be configured to be minimally intrusive to use while sleeping or minimally interfere in daily activities, may require a minimum of electrodes such as one or two, may require no electrodes to the head, may detect a seizure with motor manifestations, may alert one or more local and/or remote sites of the presence of a seizure, and may be inexpensive enough for home use.

Figure 2:
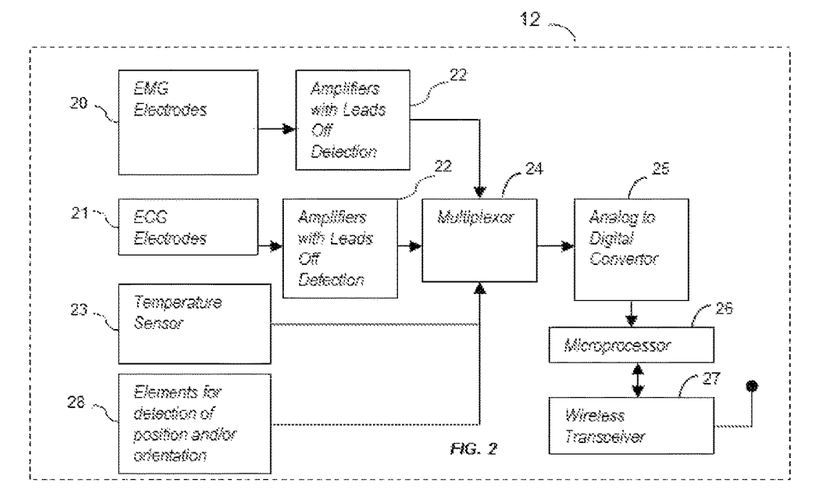
FIG. 2 illustrates one embodiment of a detection unit for a seizure detection system.

FIG. 2 illustrates an embodiment of a detection unit 12 or detector. The detection unit 12 may include EMG electrodes 20, and may also include, in some embodiments, ECG electrodes 21. The detection unit 12 may further include amplifiers with leads-off detectors 22. In some embodiments, one or more leads-off detectors may provide signals that indicate whether the electrodes are in physical contact with the person's body, or otherwise too far from the person's body to detect muscle activity, temperature, brain activity or other patient phenomena. The detection unit 12 may further include one or elements 28, such as solid state microelectromechanical (MEMS) structures, configured for detection of position and/or orientation of the detection unit 12. For example, an element 28 may include one or more micromachined inertial sensors such as one or more gyroscopes, accelerometers, magnetometers or combinations thereof.

The detection unit 12 may further include a temperature sensor 23 to sense the person's temperature and one or more orientation or position sensitive elements 28. Other sensors (not shown) may be included in the detection unit 12, as well, such as accelerometers, microphones, and oximeters. Signals from electrodes 20 and 21, temperature sensor 23, orientation and/or position sensors 28 and other sensors may be provided to a multiplexor 24. The multiplexor 24 may be part of the detection unit 12 or may be part of the base station 14 if the detection unit 12 is not a smart sensor. The signals may then be communicated from the multiplexor 24 to one or more analog-to-digital converters 25. The analog-to-digital converters may be part of the detection unit 12 or may be part of the base station 14. The signals may then be communicated to one or more microprocessors 26 for processing and analysis as disclosed herein. The microprocessors 26 may be part of the detection unit 12 or may be part of the base station 14. The detection unit 12 and/or base station 14 may further include memory of suitable capacity. The microprocessor 26 may communicate signal data and other information using a transceiver 27. Communication by and among the components of the detection unit 12 and/or base station 14 may be via wired or wireless communication.

Of course, the exemplary detection unit of FIG. 2 may be differently configured. Many of the components of the detector of FIG. 2 may be in base station 14 rather than in the detection unit 12. For example, the detection unit may simply comprise an EMG electrode 20 in wireless communication with a base station 14. In such an embodiment, A-D conversion and signal processing may occur at the base station 14. If an ECG electrode 21 is included, then multiplexing may also occur at the base station 14.

In another example, the detection unit 12 of FIG. 2 may comprise an electrode portion having one or more of the EMG electrode 20, ECG electrode 21 and temperature sensor 23 in wired or wireless communication with a small belt-worn transceiver portion. The transceiver portion may include a multiplexor 24, an A-D converter 25, microprocessor 26, transceiver 27 and other components, such as memory and I/O devices (e.g., alarm cancel buttons and visual display).

Figure 3:
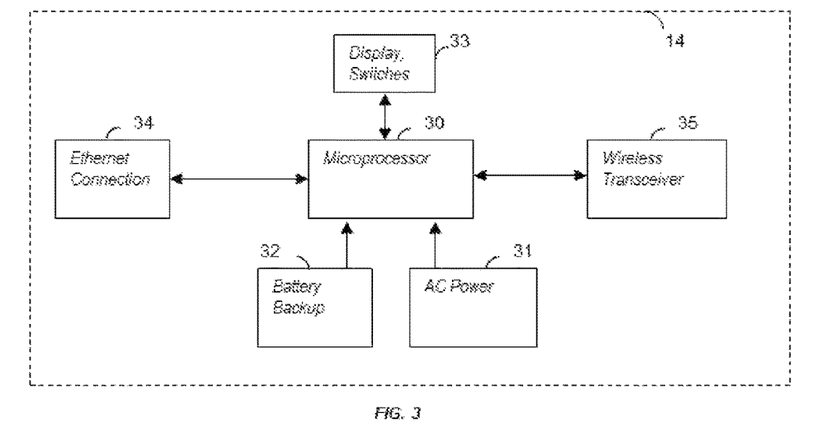
FIG. 3 illustrates one embodiment of a base station.

FIG. 3 illustrates an embodiment of a base station 14 that may include one or more microprocessors 30, a power source 31, a backup power source 32, one or more I/O devices 33, and various communications means, such as an Ethernet connection 34 and wireless transceiver 35. The base station 14 may have more processing and storage capability than the detection unit 12, and may include a larger electronic display for displaying EMG signal graphs for a caregiver to review EMG signals in real-time as they are received from the detection unit 12 or historical EMG signals from memory. The base station 14 may process EMG signals and other data received from the detection unit 12. If the base station 14 determines that a seizure is likely occurring, it may send an alert to a caregiver via transceiver 35.

Various devices in the apparatus of FIGS. 1-3 may communicate with each other via wired or wireless communication. The system 10 may comprise a client-server or other architecture, and may allow communication via network 15. Of course, the system 10 may comprise more than one server and/or client. In other embodiments, the system 10 may comprise other types of network architecture, such as a peer-to-peer architecture, or any combination or hybrid thereof.

Figure 4:
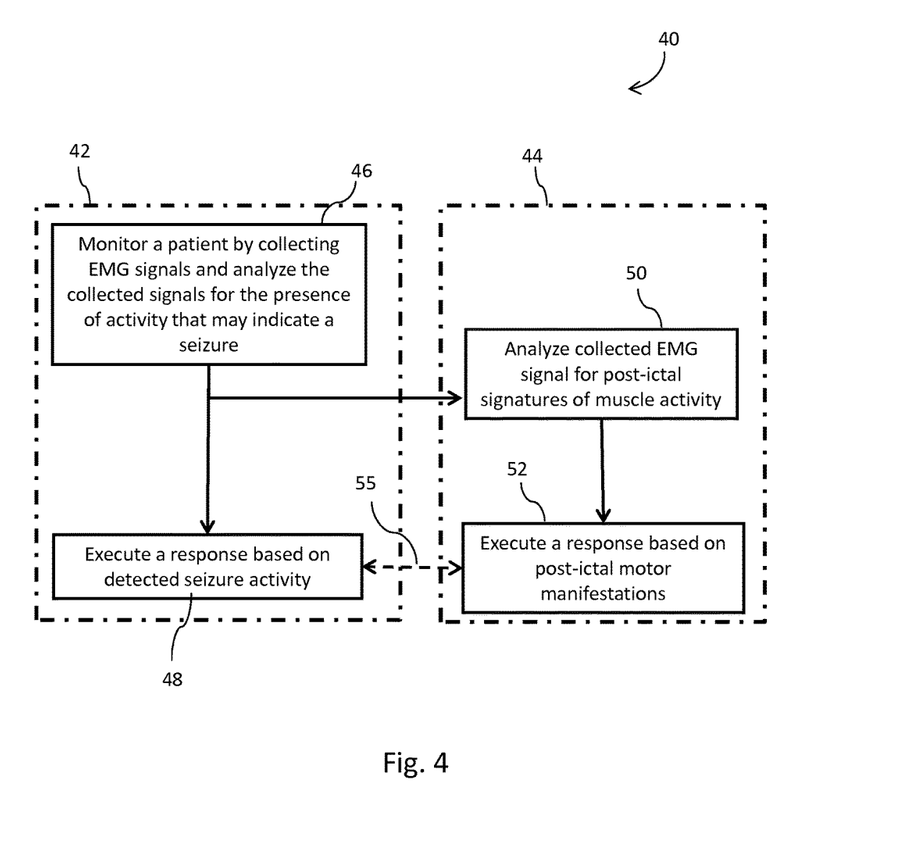
FIG. 4 illustrates one embodiment of a method for monitoring a patient for seizure activity.

FIG. 4 illustrates exemplary embodiments of a method 40 of collecting EMG signals and monitoring a patient for seizure activity. The method 40 may, in some embodiments, include collecting EMG signals, processing the signals to identify events that may indicate the presence of a seizure, and analysis of post-ictal EMG signals. In some embodiments, a patient may be monitored using EMG for the presence of motor manifestations that may typically be present during a seizure. Upon detection of those motor manifestations, the method 40 may be configured to initiate a response. Further EMG signals may also be collected. For example, those further EMG signals may be analyzed for levels of motor manifestations that may be present during post-ictal periods. In some embodiments, EMG signals collected during post-ictal periods may be analyzed for levels of motor manifestations typical of normal seizure recovery and/or for levels of motor manifestations that may be associated with abnormal recovery from a seizure. And, in some embodiments, one or more responses in addition to other responses made based on seizure detection may be made based on a level of detected post-ictal motor manifestations. More generally, upon detection of a level of post-ictal motor manifestations, the form or content of any previously issued alarms may be adjusted or an additional or new alarm transmission protocol may be initiated.

As shown in FIG. 4, the method 40 may include parts or sub-methods. A first sub-method 42 (shown by a dot-dash line) may be configured for detection of events that may indicate the presence of a seizure and for execution of responses based on the detected events. A second sub-method 44 (shown by a dot-dash line) may be configured for analysis of post-ictal motor manifestations including those that may indicate a risk of adverse effects of a seizure. Detection of seizure events in the sub-method 42 and analysis of post-ictal motor manifestations in the sub-method 44 may include collection of an electromyography signal. For example, processing of signals within the sub-methods 42, 44 may involve the system 10 and may include use of either or both of a detection unit 12 or a base station 14. In some embodiments, the sub-method 44 may execute selectively in response to a detection of one or more events that may indicate the presence of a seizure. Therefore, in some embodiments, the sub-method 44 may run intermittently based on detection of events using the sub-method 42. In other embodiments, the sub-method 44 may run continuously, but may be configured to trigger certain responses only if preceded within a certain time period by detected seizures events. Accordingly, the probability of inadvertent or false-positive initiation of an alarm based on post-ictal motor manifestations may be limited.

In some embodiments, the sub-method 44 may execute selectively in response to a detected seizure event and may further be configured to stop executing. For example, in some embodiments, the sub-method 44 may run for a predetermined period of time following detection of an event. In some embodiments the time period may last for a duration period of about 5 minutes, about 10 minutes, about 20 minutes, or about 30 minutes. In some embodiments, the sub-method 44 may run until one or more signatures of normal physiological activity are detected. For example, the sub-method 44 may execute until signal data for the patient indicates that the patient may have suitably recovered from a detected seizure event.

Although some embodiments of the sub-method 44 are not limited to particular embodiments of seizure detection, particular advantage of some embodiments of the sub-methods 44 are found when the sub-method 44 is practiced together with embodiments of the sub-methods 42 that may provide either or both of active and/or passive responses based on detected events. In those embodiments, for example, the sub-method 44 may serve to increase confidence that at least some activity may safely be treated with only a passive response. For example, execution of the sub-method 44 may provide capability to timely analyze whether the patient is recovering normally from a seizure and/or provide capability to detect rare yet potentially serious conditions that may manifest in post-seizure time periods.

Some embodiments of method 40 wherein either or both of passive and/or active responses may be initiated may include use of more than one routine as described herein. For example, in some embodiments of the sub-method 42, as indicated in the step 46, a first routine and a second routine may be executed together in a strategy to monitor a patient for various events that may be indicative of a seizure. Some of those events may be identified as including weak motor manifestations using first routines described herein and may trigger passive responses. However, methods may still provide the capability for selective and immediate identification of other events including those most closely tied to adverse effects of a seizure. For example, clonic-phase events may be tied to increased probability of adverse effects of a seizure and may be monitored using second routines as described herein. Typically, when such activity is identified with a second routine, an active response may be initiated. In addition, methods may further be configured to execute a fail-safe detection protocol to detect rare post-seizure events. For example, in some embodiments, a sub-method 42 may initiate either one or more warning responses (including passive warning responses) and/or emergency responses, but warning responses may be updated if post-ictal motor manifestations are detected (in the sub-method 44) that warrant a more aggressive response. Those methods may provide a particularly cost effective approach for seizure monitoring in some patients including those that are particularly difficult to monitor using EMG or those that may be prone to multiple weak seizure events.

In some embodiments, a sub-method 44 may operate independently of sub-method 42 to evaluate a patient for motor manifestations that may indicate an abnormal physiological condition. The method may run as an independent method to track patient physiology or in combination with other sensor signals including those that may indicate the presence of a seizure or the presence of abnormal motor manifestations. In some embodiments, those other sensor signals may be used to trigger the sub-method 44. As described herein, triggering of the sub-method 44 may be used to minimize inadvertent initiation of alarms based on false detections.

In the step 46, a patient may be monitored by collecting EMG signals and analyzing the collected EMG signals for the presence of seizure activity. Generally, in some embodiments, the overall step 46 may include any of various sub-steps in seizure detection. For example, the overall step 46 may include various sub-steps as described in detection methods covered in more detail in the references commonly owned by Applicant and incorporated herein by reference. For example, as further described in U.S. Provisional Patent Application No. 62/001,302, in some embodiments, more than one routine may execute together to analyze an electromyography signal for different seizure parts or phases. For example, some routines may be configured to be selective for clonic phase seizure activity, and other routines may be configured to be responsive to tonic phase seizure activity. In some embodiments, a first routine executed in the step 46 may include collecting EMG signals over some period of time and integrating the amplitude of collected signals within one or more consecutive or overlapping time windows within that period, and then determining if the integrated amplitude was elevated over a certain threshold for some time as may, for example, be determined if the threshold is met some number of times over a number of consecutive or overlapping time windows. Levels of EMG signal amplitude may be calculated from signal collected in one or more frequency bands and appropriate filters may be used to isolate one or more target frequency bands. Threshold levels of integrated EMG signal amplitude and/or requirements that a threshold value is maintained for a period of time may, in some embodiments, be set to make that routine responsive to motor manifestations that may be weaker than typically found in a seizure or in a seizure that is likely to be dangerous. Integration time windows may be established to improve detection of relatively weak motor manifestations. For example, in some embodiments, integration time windows for EMG signal collection may be of duration of at least about 20 milliseconds, at least about 50 milliseconds, or at least about 100 milliseconds.

Still referring to routines that may be executed in the step 46, in some embodiments, monitoring a patient for seizure activity may include a routine for isolating a plurality of frequency bands from a collected EMG signal and determining a T-squared statistical value from EMG signal amplitudes for different bands among the plurality of frequency bands. In some embodiments, a threshold T-squared statistical value may be set to make a routine responsive to weak motor manifestations that may be weaker than typically found in a seizure or in a seizure that is likely to be dangerous. In some embodiments, weights may further be applied to the plurality of bands and the relative weighting of bands may be used to improve the routine's ability for discriminating seizure events from non-seizure events. Those weights may, as described previously, be customized for an individual patient's muscle activity and may, in some embodiments, be calculated during one or more reference or training periods. For example, an inversion matrix may be determined and coefficients therein may be used to set weighting coefficients.

In some embodiments, a threshold level of EMG signal amplitude may be established based on a measurement of one or more signal amplitudes an individual may provide during a voluntary muscle contraction. Similarly, a threshold T-squared statistical value may also be set based on a measurement of one or more signal amplitudes an individual may provide during a voluntary muscle contraction. For example, in some embodiments, to capture weak motor manifestations suitable for use in some first routines, a value of a threshold signal amplitude or threshold T-squared statistical value may be about 2% to about 50% of a value achieved during a maximum voluntary contraction. In some embodiments, a threshold level may be set to make a routine responsive to weak motor manifestations including those that may be present in both tonic and clonic phase seizure events.

In some embodiments, a threshold level may be scaled in units of standard deviation above a baseline signal. For example, a baseline signal may be collected during a reference period. In some embodiments, an evaluation of whether to initiate an alarm may involve scaling the difference between a measured signal amplitude and a baseline signal amplitude in units of standard deviations and assessment of whether the number of standard deviations exceeds a threshold value (in units of standard deviations) and/or exceeds that factor for a certain time interval. And, in some embodiments, to meet the threshold, the activity may be sustained for about 1 second to about 5 seconds.

As noted above, in some embodiments, in the step 46, a combination of routines such as a first routine and second routine may be executed. In some embodiments, a combination of responses from the routines may be used to grade or stratify patient risk and determine an appropriate response to seizure activity as shown in the step 48. In some embodiments, a second routine may, for example, include higher thresholds than may be applied in a first routine. In some embodiments, routines described herein as second routines may operate individually and without another routine for seizure detection. In some embodiments, a second routine may be configured to be selective for one or more phases of seizure activity including clonic-phase activity. That activity may, even without other detected EMG signals, tend to correlate with seizure risk and may (as described in reference to Table 1 below) initiate, in some embodiments, an active response such as an emergency response. That response may, in some embodiments, include immediate execution of an emergency alarm transmission protocol.

In some embodiments, the sub-method 42 may, as shown in the step 46, initiate one or more routines that are selective for a seizure phase including the clonic-phase of a seizure. For example, the sub-method 42 may include collecting EMG signals, determining the presence of one or more characteristics of the EMG signal data, including, for example, EMG signal amplitude in one or more frequency bands and/or a T-squared statistical value calculated from EMG signal amplitude values from bands among a plurality of frequency bands, and tracking changes in the one or more characteristics over time to analyze the signal for seizure activity. In some embodiments, the characteristics may be tracked over time in a manner suitable to detect changes in the characteristics magnitude on the order of hundreds of milliseconds or less. For example, the EMG signal data may be broken up into time windows short enough to measure temporal variation of integrated EMG signal amplitude that may be present during the clonic-phase of a seizure including periods where the magnitude of EMG signal may change on the order of about 100 milliseconds. For example, in some embodiments, EMG signals may be integrated within one or more time windows and processed with a peak detection algorithm suitable for detecting transient elevations on the order of about 100 milliseconds or of shorter durations. For example, in some embodiments, integration windows may last for a duration of no more than about 10 milliseconds, no more than about 20 milliseconds, or no more than about 50 milliseconds. In some embodiments, based on counting elevations in magnitude that meet minimum and/or maximum width requirements typical of clonic-phase activity, an algorithm may be made selective for identification of bursting activity present in the clonic phase.

For example, in some embodiments, signal data may be identified as including clonic-phase bursts based on fulfilling of a minimum burst width and/or maximum burst width criterion, and if some number of bursts is detected over some period of time a positive response may be logged. That is, a routine (e.g., a second routine as described herein) may count bursts or determine a burst rate and if the number or rate of bursts exceeds a threshold a positive response may be logged. In some embodiments, a burst envelope may be generated and the burst envelope may impact a signal-to-noise ratio (SNR) threshold that may be used to identify bursts. For example, with a simple peak detect method, bursts may be qualified by meeting a threshold SNR of about 1.25 to about 20 and by meeting a minimum threshold for burst width of about 25 to about 75 milliseconds and maximum burst width threshold of no greater than about 250 milliseconds to about 400 milliseconds. Bursts may then be counted and a number of bursts or rate of bursts may be determined. For example, a positive routine response (e.g., a response indicating seizure activity) may then, for some patients, be triggered if between about 2 to about 6 bursts are measured within a time window of about 1 second or if another suitable number of bursts are counted in some other appropriate time window.

A threshold number of burst count for a patient may be the same or different than an expected number of physiological events that may produce bursts. For example, depending on a SNR threshold level and/or other thresholds, at least some of the physiological events associated with bursts may not be detected, but a threshold number of bursts may still be detected and may be used to trigger a positive routine response. For example, in some embodiments, a positive routine response may be made if at least about 2 to about 6 bursts are measured within a time window of about 2 to about 5 seconds. And, in some embodiments, a certainty value may be assigned to bursts. For example, a processor may be configured to detect bursts of EMG signal data, assign certainty values to individual burst members among the detected bursts, and determine a burst count contribution to seizure detection based on a number of said detected bursts weighted as a function of the certainty value assigned to the individual burst members.

In some embodiments, a first routine suitable for identifying weak motor manifestations may be responsive to seizure activity derived from either or both of a tonic phase and/or clonic phase of a seizure. And, in some embodiments, that first routine may be combined with one or more other routines including at least one that is selective for clonic-phase seizure activity. Therefore, tonic-only events may be selectively identified by looking at a combination of responses from the two routines. For example, if the first routine shows a positive response and a clonic-selective routine shows a negative response, it may be deemed that only tonic-phase activity was detected. Likewise, the second routine may be selective for clonic activity. Therefore, by looking at the relative response in the first and second routines over time, tonic, clonic, tonic-clonic as well as various multi-part seizures may not only be detected but selectively detected and used to characterize collected signal data. For example, where selective detection of a phase is made, the phase may be deemed to have occurred without ambiguity.

Based on the presence of a certain type of seizure, an appropriate response may be initiated including, for example, selection and execution of a warning, emergency, ambulance, and/or other transmission protocol or combination of protocols thereof. For example, in some embodiments, upon identification of a positive response in one or more monitoring routines, a method may be configured to initiate a warning period for further analysis of patient activity or to only issue a warning message but not an emergency alarm message. For example, a positive response in one or more monitoring routines may be used to determine that a warning event was detected (e.g., an event that may not warrant an emergency response), and a response to such detection may be to collect further information to more fully evaluate the event or to initiate a warning protocol which may, for example, be a protocol that may be executed without patient intrusion. Some methods including protocols for treatment of events that may initiate warning signals or transmission protocols are, for example, described in Applicant's Provisional Patent Application No. 62/001,302 incorporated herein by reference.

By way of further example, execution of a first routine responsive to even weak motor manifestations (routine 1) and execution of a second routine configured to identify clonic-phase bursts (routine 2) may be used to classify detected activity and initiate a response as shown in Table 1.

TABLE 1

| Event | Routine 1 - Status | Routine 2 - Status | Classification | Status/Transmission Protocol (as may be executed in some embodiments) |
| --- | --- | --- | --- | --- |
| A) | Negative | Negative | non-seizure | no transmission |
| B) | Positive | Negative | tonic-phase or tonic/non-seizure | warning protocol (automatic message only) |
| C) | Negative | Positive | clonic - phase | emergency protocol (Que alarm message and send data - enable review of EMG data by a remote user and/or verification of event status) |
| D) | Positive | Positive | clonic - phase | emergency status (automatic message along with EMG data to qualified individual) |

The sub-method 42 may, in some embodiments, be configured to initiate an alarm response prior to collection of post-ictal signatures of muscle activity. For example, at least for some detected events, an alarm response may be initiated such as may include, e.g., contacting a caregiver with instructions to check on a patient, calling the patient, and/or sending an ambulance to a patient location. In some embodiments, that alarm response may be initiated immediately. However, in some embodiments, an alarm response may be queued for transmission and a system may delay alarm execution for some period. For example, in some embodiments, an alarm may be delayed for up to about 30 seconds, 60 seconds, 300 seconds or another delay period.

In some embodiments, a particular response protocol may be based on a profile for a patient. For example, for some patients a profile may specify whether an alarm response is issued immediately or queued for submission following some delay. In some embodiments, a monitoring system may be configured to enable a patient to update their status based on one or more selectable profiles. For example, a patient may be given an option to select one or more different monitoring settings based, for example, on whether the patient is in bed sleeping, whether the patient is at home alone, or if the patient is at home with another person. And, depending on whether the patient selects one of those options, the system may select different settings and/or thresholds. Furthermore, for a certain response or group of responses, a monitoring system may, for example, select a transmission protocol that depends on a selected option.

The execution of a sub-method 44 may, in some embodiments, be initiated upon detection of activity identified in the sub-method 42. In the sub-method 44, as shown in the step 50, EMG signals may be collected and analyzed for the presence of post-ictal muscle activity. The step 50 may include analysis of collected EMG signal to determine if a level of post-ictal motor manifestations is present that may indicate that a patient is at heightened risk of adverse effects of a seizure. For example, following a seizure, a patient may experience a degree of central nervous system depression. A patient experiencing that effect may be characterized by low levels of motor manifestations. In some embodiments, certain levels of motor manifestation may be used to establish that the patient is at risk of adverse effects of a seizure including SUDEP.

In some embodiments, a threshold value of EMG signal amplitude or some other suitable characteristic of muscle activity measurable with EMG may be set and EMG signal may be compared to the threshold value to monitor a patient for post-ictal motor manifestations. Periods in which collected EMG signal may be above the threshold level may be classified as periods of elevated post-ictal motor manifestations.

Periods of elevated post-ictal motor manifestations and intervening periods may be determined and used to evaluate a level of muscle activity for a patient. For example, in some embodiments, a patient may be deemed to be experiencing a level of muscle activity consistent with central nervous system depression if an extended period of time is identified between periods of elevated post-ictal motor manifestations or if other metrics of muscle activity support a finding that the patient is showing low muscle activity. For example, in some embodiments, various metrics may be used individually or in combination to identify a level of muscle activity the relative presence or absence of which may be used to evaluate a patient's recovery from a seizure event. In some embodiments, metrics for identification of a level of muscle activity may include, by way of nonlimiting example, number or rate of identified periods of elevated post-ictal motor manifestations, duration between periods of elevated post-ictal motor manifestations, average duration between periods of elevated post-ictal motor manifestations, and combinations thereof. In some embodiments, a suitable response may be initiated if, over some window of time, abnormal muscle activity is determined. For example, if an average duration between periods of elevated post-ictal motor manifestations is abnormally high a response may be initiated. In some embodiments, trends over time for selected metrics may be determined. For example, if an average duration between periods of elevated post-ictal motor manifestations is found to be increasing or changing in a characteristic way associated with initial stages identified with SUDEP, the system may respond accordingly, such as with execution of an emergency response.

Figure 5:
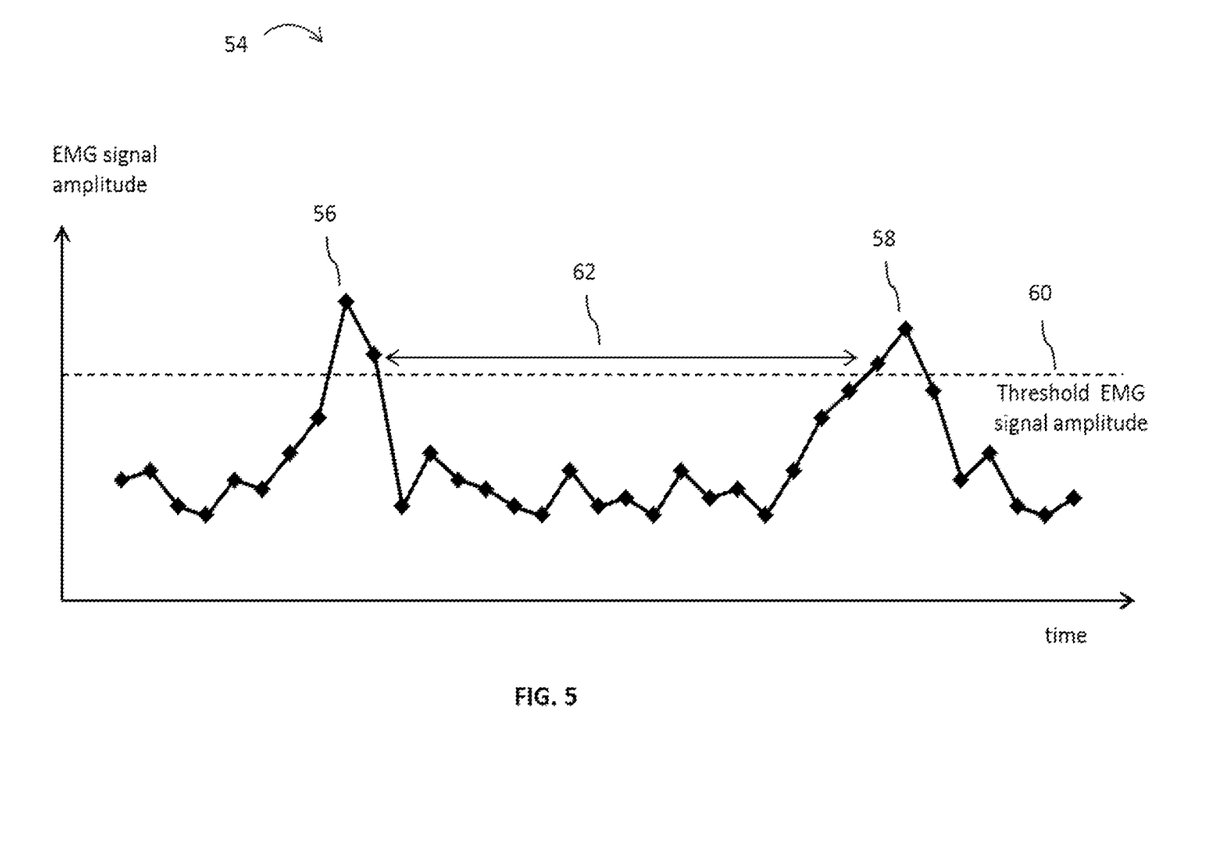
FIG. 5 illustrates model EMG data.

In some embodiments, one or more peak detection algorithms may be executed as part of the sub-method 44. Identified peaks may be processed and it may be determined if the peaks meet a required set of one or more thresholds to identify the peaks as periods of elevated post-ictal motor manifestations. Suitable peak detection, data smoothing, and/or baseline correction procedures may also be implemented. FIG. 5 illustrates model data (54) for EMG signal amplitude over time. As shown therein, for explanation purposes only, the regions 56 and 58 are shown to exceed an EMG threshold level (shown by the dashed line 60). Therefore, two periods of elevated post-ictal motor manifestations are shown within the time period of FIG. 5. A duration interval 62 between the regions 56 and 58 of elevated EMG amplitude is also shown therein.

In some embodiments, levels of patient muscle activity collected in a post-ictal monitoring period may be compared against levels of activity measured for the patient during a reference period. For example, EMG signals may be collected during a reference period when a patient is awake or during a reference period wherein the patient is asleep or transitioning into a period of sleep. Typical levels of muscle activity may be identified from the reference period and used to determine threshold values or settings suitable for identifying periods of elevated post-ictal motor manifestations. For example, a certain threshold value may be set such that during a normal period of seizure recovery a patient resting in bed may experience no less than about 5 to about 10 periods of elevated post-ictal motor manifestations over a time period of about 1 minute. If, during a certain monitoring time period, a patient is found to experience less than about 5 to about 10 periods of elevated post-ictal motor manifestations, the patient may be deemed to be experiencing atypical recovery. And, for some number of post-ictal motor manifestations, a suitable level may be reached to indicate atypical recovery and a response may be initiated. In some embodiments, typical levels of muscle activity may be recorded for a patient during and after a seizure. And, as more data is collected for a patient during those periods, settings for identifying atypical post-ictal motor manifestations may be updated.

In some embodiments, signal amplitude that is measured during a post-ictal monitoring period may be scaled in units of standard deviation above a baseline signal. For example, an evaluation of whether a period of elevated post-ictal motor manifestations is present may involve scaling the difference between a measured signal amplitude and a baseline signal amplitude in units of standard deviations and assessment of whether the number of standard deviations exceeds a threshold value (in units of standard deviations) and/or exceeds that factor for a certain time interval.

In some embodiments, a threshold signal amplitude may be set, and if EMG signal of magnitude greater than the threshold signal amplitude is found for a time period, then a period of elevated post-ictal motor manifestations may be deemed present. For example, in some embodiments, a motor manifestation suitable to produce a signal of magnitude of about 5 μV to about 400 μV at a skin surface may be sufficient to qualify the signal as a period of elevated post-ictal motor manifestations. And, in some embodiments, to help differentiate the signal from sources of noise it may, in some embodiments, be required that the signal magnitude is maintained for at least about 20 to about 50 milliseconds in order to be qualified as a period of elevated post-ictal motor manifestation.

In some embodiments, if periods of elevated post-ictal motor manifestations are not detected for a period of about 10 seconds to about 240 seconds, it may be deemed that the patient is experiencing abnormal levels of muscle activation. For example, the patient may be deemed to be at risk of SUDEP and as shown in the step 52, an alarm response may then be initiated. Of course, if risk of SUDEP is deemed to be significant an aggressive alarm protocol may be initiated. For example, in some embodiments, attempts to contact the patient and/or other local caregivers may be made if post-ictal motor manifestations are identified that indicated CNS depression. In addition, in some embodiments, identification of CNS depression may initiate an ambulance alarm transmission protocol particularly if the patient is known to typically live alone or had previously selected from a selectable setting that they were alone.

In some embodiments, periods of elevated post-ictal motor manifestations may be tracked over time, and if less than some critical number of elevated post-ictal motor manifestations are detected, it may be deemed that the patient is experiencing abnormal levels of muscle activation. In some embodiments, if either a critical duration period between periods of elevated post-ictal motor manifestations or if less than some critical number of elevated post-ictal motor manifestations are detected over time, then a patient may be deemed to be at risk of adverse effects of a seizure.

In some embodiments, as shown in the steps 48 and 52, an alarm response may depend on either or both of the detection of seizure activity and/or post-ictal motor manifestations indicating a risk of adverse effects of a seizure. A monitoring system may log the status of alarms executed in either or both of the steps 48 and 52 of sub-methods 42 and 44. And, for example, a warning alarm may be initiated by the sub-method 42, but at some other time post-ictal muscle activity indicating adverse risks may be detected. In that case, for example, the system may issue a new alarm transmission protocol such as, for example, a protocol associated with an emergency or ambulance response. More generally, in some embodiments, a monitoring system may update an overall alarm status as more information is obtained about the overall state of the patient. An alarm message may also include information regarding characteristics of other alarms that may have been sent. For example, as indicated by the dashed arrow 55, sub-methods 42 and 44 may share information and data from each of the aforementioned sub-methods may be integrated together to provide all available information to a caregiver.

Figure 6:
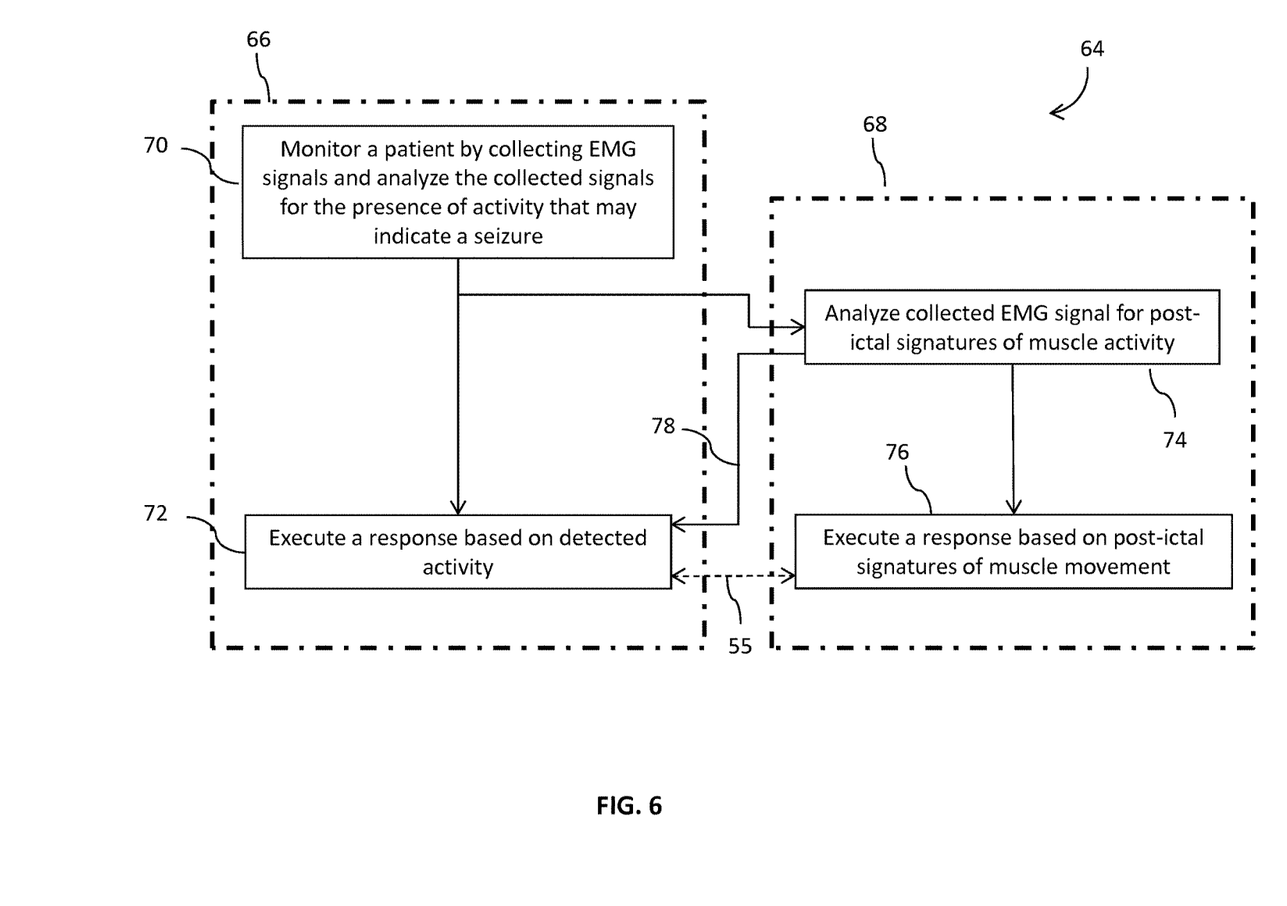
FIG. 6 illustrates another embodiment of a method for monitoring a patient for seizure activity.

FIG. 6 illustrates exemplary embodiments of a method 64 for collecting EMG signals and monitoring a patient for seizure activity. The method 64 may, in some embodiments, include collecting EMG signals, processing the signals to identify events that may indicate the presence of a seizure, and execution of one or more sub-method routines to examine a patient for post-ictal motor manifestations including those that may be related to an increased risk of adverse effects of a seizure. In some embodiments of method 64, in addition to monitoring the patient for post-ictal motor manifestations that may indicate an increased risk of adverse effects of a seizure, one or more routines may examine if post-ictal motor manifestations are present that may be found during a normal post-seizure recovery. And, if signatures of normal post-seizure recovery are identified to be present, the method 64 may, in some embodiments, be configured to adjust an existing alarm response including, for example, a response initiated in response to previously detected seizure activity. Or, for example, if a normal post-seizure recovery is identified, a protocol or routine may then terminate without executing one or more actions that otherwise may have been executed. For example, in some embodiments, an alarm may be queued to be sent at some later time, and identification of a normal post-seizure recovery may be used to prevent the scheduled alarm from executing. Accordingly, in some embodiments, a queued alarm may be terminated based on positive detection of normal motor activity. Alternatively, if an alarm was already sent, appropriate caregivers may be informed that the patient had appeared to have recovered from the seizure. The sub-method 68 may, in some embodiments, as shown in the step 76, trigger an alarm response if, for example, muscle activity levels in time periods of seizure recovery are abnormal. The sub-method may also terminate or adjust some actions (as shown with communication arrow 78 described below) if normal post-seizure recovery is detected with high certainty.

The method 64 may include a sub-method 66 configured to monitor the patient for seizure activity. One or more routines may be executed in a step 70 of sub-method 66 to identify activity that may indicate the presence of a seizure. Upon identification of seizure activity, one or more responses including, for example, execution of one or more alarm transmission protocols may be initiated as shown in the step 72. In addition, as shown in the step 74 of the sub-method 68, detected seizure activity may initiate execution of one or more routines associated with detection of muscle activity associated with post-seizure recovery. Those routines may, in some embodiments, include both one or more routines to examine EMG signals for atypical seizure recovery and one or more routines looking for activity typical of normal muscle movements.

When examining an EMG signal for characteristics of normal post-seizure recovery there may, for some patients, be a risk that further seizure activity is incorrectly identified as part of the normal post-seizure recovery. That concern may not be applicable to some of the routines and/or responses initiated in the sub-method 44 of the method 40. For example, in some embodiments of the method 40 post-ictal motor manifestations may only be analyzed for abnormal recovery, such as may, for example, be characterized by an absence of periods of elevated post-ictal motor manifestations. The absence of periods of elevated post-ictal motor manifestations may generally not be confused with additional seizure activity. However, referring to the method 64, and particular embodiments where routines for identifying post-ictal motor manifestations that may be part of post-seizure recovery are executed, risk of incorrectly characterizing elevated post-ictal motor manifestations and seizure activity may be considered. Particularly, settings may be established to differentiate repetitive seizure activity from periods of elevated post-ictal motor manifestations. Typically, seizure activity may be characterized by a much higher amplitude value than other amplitude values during post-ictal periods. Accordingly, amplitude thresholds may generally be readily set to differentiate repetitive seizure activity from periods of post-ictal motor manifestations.

As shown by a communication signal 78, EMG signal analyzed for post-ictal signatures of muscle activity (step 74) may be used to update a response that may have been issued based on detected seizure activity (steps 70 and 72 of sub-method 66). For example, as described previously, a response to some seizure events may be to queue a signal for later transmission after some period of time. During the intervening time between when the signal is queued and the time of transmission, the patient may show normal recovery from the detected seizure event. In that case, the event, which may, for example, have been a weak motor manifestation, may be determined to have come and gone without the need for emergency intervention. Therefore, the arrow 78 may represent a communication signal between the sub-methods 66 and 68 where post-ictal signatures alter the response of previously detected activity. And, particularly, the communication signal 78 may include a signal to cancel a previously queued response. More generally, other signals may be passed between processors involved in the sub-methods 66 and 68 as shown by the communication signal arrow 55.

Figure 7:
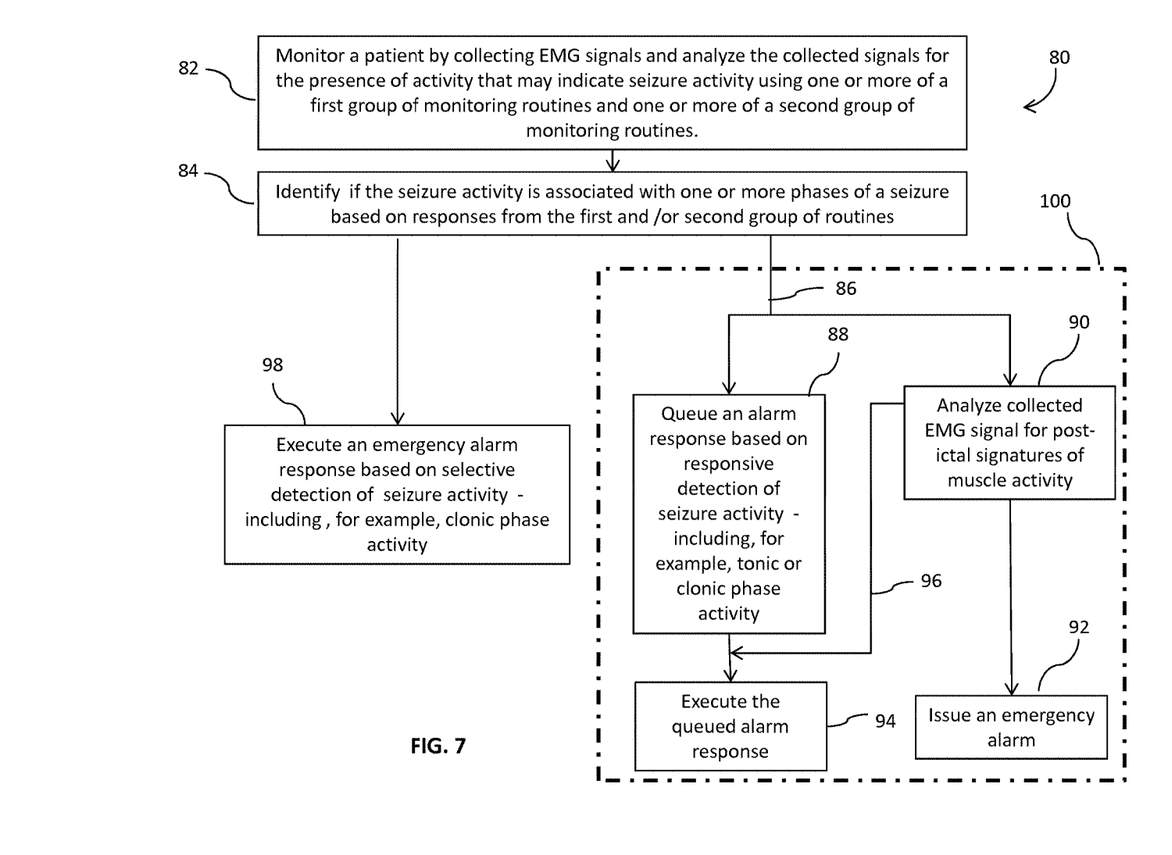
FIG. 7 illustrates still another embodiment of a method for monitoring a patient for seizure activity.

FIG. 7 illustrates exemplary embodiments of a method 80 where EMG signals are collected and analyzed for seizure activity using a combination of monitoring routines. The patient may be monitored for seizure activity as shown in the step 82 using a combination of routines. As shown in the step 84, specific types of seizure activity may be identified. For example, one or more routines in a first group of routines may be configured to detect weak motor manifestations. In some embodiments, that first group of routines may be responsive to both tonic and clonic periods of seizure activity. In addition, one or more routines in the second group of routines may be configured to be selective in responding to clonic-phase activity.

Referring to the routine path 86, in some embodiments, in response to an event that may correspond to either of tonic or clonic-phase activity, a transmission protocol may be initiated. For example, an alarm may be queued for transmission. That is, the system may respond, as shown in the step 88, by establishing that an alarm may be sent to a caregiver after a certain delay. Within that delay period, further EMG signal may be collected and analyzed for seizure activity. And, in some embodiments, a decision may be made if the further collected EMG signal supports or contradicts a finding that a seizure is present and/or if the patient shows one or more characteristics associated with post-seizure recovery. For example, in some embodiments, as shown in the step 90, one or more routines may be initiated to examine the further collected EMG signal for muscle activity, including, for example, activity that may be associated with post-seizure recovery and/or abnormal recovery from a seizure. In some embodiments, as shown in the step 92, an emergency response may be initiated if one or more routines for analysis of post seizure muscle activity indicate an abnormal recovery from an expected seizure event.

As shown in the step 94, an alarm may be sent after a period of collecting additional EMG signal. However, during a delay period between queuing the alarm and alarm execution, intervening events may act to prevent alarm execution. For example, in some embodiments, following detection of seizure activity the EMG signal may show signs of normal muscle movements that may indicate, for example, that the detected event was either a false detection or that the patient had suitably recovered from the seizure event. In some embodiments, as shown by the communication signal 96, a routine for analysis of normal post-ictal activity may give a positive response, and the queued alarm may be canceled or adjusted based on that communication.

In some embodiments, the method 80 may include, as shown in the step 98, a protocol for responding to a positive detection from one or more routines among the second group of routines. For example, a positive response to a second routine may as shown in the step 84 identify that clonic-phase activity is present. For example, the clonic-phase may be found to be selectively present and in response (as shown in the step 98) an emergency alarm response may be executed. In some embodiments, for example, an emergency transmission protocol may be immediately sent without delay upon identification of the clonic-phase activity.

In another embodiment, the steps indicated in the dot-dash line 100 may be used in combination with seizure monitoring methods as a way of further qualifying that a seizure event may demand a certain response. For example, a signal may indicate that a patient may have experienced a seizure, and the detection may trigger a period for further analysis and/or verification of the detected activity prior to initiating one or more alarm protocols.

Generally, the devices of a seizure detection system may be of any suitable type and configuration to accomplish one or more of the methods and goals disclosed herein. For example, a server may comprise one or more computers or programs that respond to commands or requests from one or more other computers or programs, or clients. The client devices may comprise one or more computers or programs that issue commands or requests for service provided by one or more other computers or programs, or servers. The various devices in FIG. 1, e.g., 12, 13, 14, 16, 17, 18 and/or 19, may be servers or clients depending on their function and configuration. Servers and/or clients may variously be or reside on, for example, mainframe computers, desktop computers, PDAs, smartphones (such as Apple's iPhone™, Motorola's Atrix™ 4G, Motorola's Droid™, Samsung's Galaxy S™, Samsung's Galaxy Note™, and Research In Motion's Blackberry™ devices), tablets (such as Sony's Xperia™, Samsung's Galaxy Tab™, and Amazon Kindle™) netbooks, portable computers, portable media players with network communication capabilities (such as Microsoft's Zune HD™ and Apple's iPod Touch™ devices), cameras with network communication capabilities, smartwatches, wearable computers, and the like.

A computer may be any device capable of accepting input, processing the input according to a program, and producing output. A computer may comprise, for example, a processor, memory and network connection capability. Computers may be of a variety of classes, such as supercomputers, mainframes, workstations, microcomputers, PDAs and smartphones, according to the computer's size, speed, cost and abilities. Computers may be stationary or portable, and may be programmed for a variety of functions, such as cellular telephony, media recordation and playback, data transfer, web browsing, data processing, data query, process automation, video conferencing, artificial intelligence, and much more.

A program may comprise any sequence of instructions, such as an algorithm, whether in a form that can be executed by a computer (object code), in a form that can be read by humans (source code), or otherwise. A program may comprise or call one or more data structures and variables. A program may be embodied in hardware or software, or a combination thereof. A program may be created using any suitable programming language, such as C, C++, Java, Perl, PHP, Ruby, SQL, and others. Computer software may comprise one or more programs and related data. Examples of computer software include system software (such as operating system software, device drivers and utilities), middleware (such as web servers, data access software and enterprise messaging software), application software (such as databases, video games and media players), firmware (such as device specific software installed on calculators, keyboards and mobile phones), and programming tools (such as debuggers, compilers and text editors).

Memory may comprise any computer-readable medium in which information can be temporarily or permanently stored and retrieved. Examples of memory include various types of RAM and ROM, such as SRAM, DRAM, Z-RAM, flash, optical disks, magnetic tape, punch cards, EEPROM. Memory may be virtualized, and may be provided in, or across one or more devices and/or geographic locations, such as RAID technology. An I/O device may comprise any hardware that can be used to provide information to and/or receive information from a computer. Exemplary I/O devices include disk drives, keyboards, video display screens, mouse pointers, printers, card readers, scanners (such as barcode, fingerprint, iris, QR code, and other types of scanners), RFID devices, tape drives, touch screens, cameras, movement sensors, network cards, storage devices, microphones, audio speakers, styli and transducers, and associated interfaces and drivers.

A network may comprise a cellular network, the Internet, intranet, local area network (LAN), wide area network (WAN), Metropolitan Area Network (MAN), other types of area networks, cable television network, satellite network, telephone network, public networks, private networks, wired or wireless networks, virtual, switched, routed, fully connected, and any combination and subnetwork thereof. The network may use a variety of network devices, such as routers, bridges, switches, hubs, repeaters, converters, receivers, proxies, firewalls, translators and the like. Network connections may be wired or wireless, and may use multiplexers, network interface cards, modems, IDSN terminal adapters, line drivers, and the like. The network may comprise any suitable topology, such as point-to-point, bus, star, tree, mesh, ring and any combination or hybrid thereof.

Wireless technology may take many forms such as person-to-person wireless, person-to stationary receiving device, person-to-a-remote alerting device using one or more of the available wireless technology such as ISM band devices, WiFi, Bluetooth, cell phone SMS, cellular (CDMA2000, WCDMA, etc.), WiMAX, WLAN, and the like.

Communication in and among computers, I/O devices and network devices may be accomplished using a variety of protocols. Protocols may include, for example, signaling, error detection and correction, data formatting and address mapping. For example, protocols may be provided according to the seven-layer Open Systems Interconnection model (OSI model), or the TCP/IP model.

Although the disclosed method and apparatus and their advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition, or matter, means, methods and steps described in the specification. For example, any feature described for one embodiment may be used in any other embodiment. Use of the word "include," for example, should be interpreted as the word "comprising" would be, i.e., as open-ended. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods or steps.

What is claimed is:

1. A method of monitoring a patient for seizure activity and controlling one or more alarm responses, the method comprising:
   providing a mobile EMG detection unit in wireless communication with one or more caregiver devices, said mobile EMG detection unit including one or more EMG electrodes;
   disposing said mobile EMG detection unit on or near one or more patient muscles;
   monitoring a patient by collecting electrical signals of muscle activation in order to provide a collected EMG signal using said mobile EMG detection unit;
   processing said collected EMG signal using either said mobile EMG detection unit or said one or more caregiver devices to detect and classify seizure activity of the patient using a first EMG seizure detection routine configured to determine an EMG signal amplitude and compare said EMG signal amplitude to a threshold level of EMG signal amplitude, and a second EMG seizure detection routine that responds selectively to clonic-phase burst activity based on detection of a threshold number of bursts, said bursts identified based on meeting a minimum burst width threshold and a maximum burst width threshold during a first time period;
   initiating a first response if said seizure activity is detected during said first time period;
   wherein said first response includes a selection and an execution of either a first alarm protocol configured to terminate passively or a second alarm protocol configured to initiate an immediate emergency response including wirelessly sending a message to at least one of said one or more caregiver devices, said selection based upon the classification of seizure activity;
   initiating processing of said collected EMG signal to determine a level of motor manifestations in a second time period; and
   initiating a second response if said level of motor manifestations in the second time period corresponds to a level of post-ictal motor manifestations indicative of an increased risk of adverse effects of a seizure.

2. The method of claim 1 wherein said threshold level of EMG signal amplitude is about 2% to about 50% of an EMG signal amplitude level that may be achieved by said patient during a maximum voluntary contraction.

3. The method of claim 1 wherein said first response includes sending a message to at least one of said one or more caregiver devices that a warning event was detected, said first response initiated if said first EMG seizure detection routine detects said seizure activity.

4. The method of claim 1 wherein said first response is configured to terminate passively if within one or more time periods following said first time period further collected EMG signal show no evidence of seizure activity.

5. The method of claim 1 wherein the determining of said level of motor manifestations in said second time period comprises:
   analyzing EMG signal collected within said second time period for periods of elevated post-ictal motor manifestations by comparing said EMG signal to a threshold condition; and
   determining a duration interval between adjacent elevated post-ictal motor manifestations.

6. The method of claim 5 wherein said level of motor manifestations in said second time period is deemed to correspond to said level of post-ictal motor manifestations indicative of increased risk of adverse effects of a seizure if said duration interval is between about 10 seconds to about 240 seconds; and
   wherein said threshold condition includes exceeding a voltage of about 10 µV to about 250 µV above a baseline level for said patient.

7. The method of claim 1 wherein the determining of said level of motor manifestations in said second time period comprises:
   analyzing EMG signal collected within said second time period for periods of elevated post-ictal motor manifestations by comparing said EMG signal to a threshold condition; and
   determining a number of said periods of elevated post-ictal motor manifestations present.

8. The method of claim 7 wherein said level of motor manifestations is deemed indicative of said increased risk of adverse effects of a seizure if said number of said periods of elevated post-ictal motor manifestations is less than a threshold number.

9. The method of claim 1 wherein said second response includes initiation of an ambulance alarm transmission protocol.

10. The method of claim 1 wherein said selection of either of said first alarm protocol or said second alarm protocol depends on whether said patient is in one of a selectable number of patient states.

11. The method of claim 10 wherein said patient states include at least two patient states selected from a state where said patient is awake, a state where said patient is sleeping, a state where said patient is at home in the presence of another person, and a state where said patient is at home alone.

12. The method of claim 1 further comprising initiating a second response if said level of motor manifestations determined in said second time period is associated with a level of post-ictal motor manifestations indicative of normal recovery from a seizure.

13. A method of monitoring a patient for seizure activity and controlling one or more alarm responses, the method comprising:
   providing a mobile EMG detection unit in wireless communication with one or more caregiver devices, said mobile EMG detection unit including one or more EMG electrodes;
   disposing said mobile EMG detection unit on or near one or more patient muscles;
   monitoring a patient by collecting electrical signals of muscle activation in order to provide a collected EMG signal using said mobile EMG detection unit
   processing said electrical signals of muscle activation during a first time period to detect seizure activity;

initiating a first response based on detection of said seizure activity, said first response including sending one or more messages to at least one of said one or more caregiver devices;

wherein said first response further includes initiation of an EMG sub method configured for determining a level of motor manifestations in a time period following detection of seizure activity; and initiating a second response based on said level of motor manifestations, the second response updating at least one of said one or more messages;

wherein determining said level of motor manifestations in said time period following detection of seizure activity comprises:

analyzing EMG signal collected during said time period following detection of seizure activity for periods of elevated post-ictal motor manifestations by comparing the EMG signal to a threshold condition and determining a number of said periods of elevated post-ictal motor manifestations present; and comparing a number of said periods of elevated post-ictal motor manifestations to a first threshold number of periods of elevated post-ictal motor manifestations and to a second threshold number of periods of elevated post-ictal motor manifestations;

wherein said level of motor manifestations is considered to achieve level of post-ictal motor manifestations indicative of an increased risk of adverse effects of a seizure if the number of said periods of elevated post-ictal motor manifestations is less than said first threshold number;

wherein said level of motor manifestations is considered to achieve a level of post-ictal motor manifestations indicative of normal recovery from a seizure if the number of said periods of elevated post-ictal motor manifestations is greater than said second threshold number.

14. The method of claim 13 further comprising determining a periodicity condition for said periods of elevated post-ictal motor manifestations;

wherein said level of post-ictal motor manifestations indicative of normal recovery from a seizure is deemed present only if said periodicity condition is achieved.

15. The method of claim 1 wherein said second time period lasts for a predetermined period of time following said first response.

16. The method of claim 15 wherein said predetermined period of time is about 5 minutes to about 10 minutes.

17. The method of claim 13 wherein said time period following detection of seizure activity lasts for a predetermined period of time following said first response.

18. The method of claim 17 wherein said predetermined period of time is about 5 minutes to about 10 minutes.

19. The method of claim 13 wherein said first response depends on whether said patient is in one of a selectable number of patient states.

20. The method of claim 19 wherein said patient states include at least two patient states selected from a state where said patient is awake, a state where said patient is sleeping, a state where said patient is at home in the presence of another person, and a state where said patient is at home alone.

* * * * *